US009440907B2

(12) United States Patent
Ishibashi et al.

(10) Patent No.: US 9,440,907 B2
(45) Date of Patent: *Sep. 13, 2016

(54) PRODUCTION METHOD FOR 2-ALKENYLAMINE COMPOUND

(75) Inventors: Yoshitaka Ishibashi, Minato-ku (JP); Naoya Fukumoto, Minato-ku (JP); Masato Kitamura, Nagoya (JP)

(73) Assignees: SHOWA DENKO K.K., Tokyo (JP); NATIONAL UINVERSITY CORPORATION NAGOYA UNIVERSITY, Aichi (JP)

(*) Notice: Subject to any disclaimer, the term of this patent is extended or adjusted under 35 U.S.C. 154(b) by 0 days.

This patent is subject to a terminal disclaimer.

(21) Appl. No.: 14/237,758

(22) PCT Filed: Aug. 29, 2012

(86) PCT No.: PCT/JP2012/071855
§ 371 (c)(1),
(2), (4) Date: Feb. 7, 2014

(87) PCT Pub. No.: WO2013/031839
PCT Pub. Date: Mar. 7, 2013

(65) Prior Publication Data
US 2014/0171687 A1    Jun. 19, 2014

(30) Foreign Application Priority Data
Aug. 31, 2011    (JP) .................. 2011-188545

(51) Int. Cl.
C07C 209/68    (2006.01)
C07C 209/16    (2006.01)
C07C 209/18    (2006.01)
B01J 31/22    (2006.01)

(52) U.S. Cl.
CPC .......... *C07C 209/68* (2013.01); *B01J 31/2217* (2013.01); *C07C 209/16* (2013.01); *C07C 209/18* (2013.01); *B01J 2231/341* (2013.01); *B01J 2531/821* (2013.01); *B01J 2531/822* (2013.01); *B01J 2531/827* (2013.01)

(58) Field of Classification Search
CPC .................................................. C07C 209/68
See application file for complete search history.

(56) References Cited

U.S. PATENT DOCUMENTS

| 5,578,740 A | 11/1996 | Au et al. | |
|---|---|---|---|
| 5,908,943 A * | 6/1999 | Au et al. | 549/559 |
| 2005/0203317 A1 | 9/2005 | Kitamura et al. | |
| 2006/0004013 A1 | 1/2006 | Kimura et al. | |
| 2007/0213549 A1 | 9/2007 | Ishii et al. | |
| 2009/0054689 A1 | 2/2009 | Carreira | |
| 2014/0200345 A1* | 7/2014 | Ishibashi et al. | 544/178 |

FOREIGN PATENT DOCUMENTS

| JP | 8-283209 A | 10/1996 |
|---|---|---|
| JP | 10-511721 A | 11/1998 |
| JP | 2005-289977 A | 10/2005 |
| JP | 2007-238562 A | 9/2007 |
| JP | 2009-46452 A | 3/2009 |
| JP | 2011-140456 A | 7/2011 |
| TW | I335816 B | 1/2011 |

OTHER PUBLICATIONS

Gill et al. "Photochemical Properties of the Cyclopentadienyl($\eta$6-benzene)ruthenium (II) cation. The Synthesis and Reactions of a Synthetically Useful Intermediate: The Cyclopentadienyltris(acetonitril)ruthenium(II) cation" Organometallics, 1982, 1, 485-488.*
Yi Wang et al., "Highly Regio- and Enantioselective Palladium-Catalyzed Allylic Amination with Sodium Diformylamide", J. Org. Chem. 2001, pp. 3238-3241, vol. 66, No. 9.
David A. Evans et al., "Application of Chiral Mixed Phosphorous/Sulfur Ligands to Palladium-Catalyzed Allylic Substitutions", J. Am. Chem. Soc. 2000, pp. 7905-7920, vol. 122, No. 33.
P. Andrew Evans et al., "Regioselective Rh-Catalyzed Allylic Amination/Ring-Closing Metathesis Approach to Monocyclic Azacycles: Diastereospecific Construction of 2,5-Disubstituted Pyrrolines", Organic Letters 1999, pp. 1929-1931, vol. 1, No. 12.
Robert Weihofen et al., "Salt-Free Iridium-Catalyzed Asymmetric Allylic Aminations with N,N-Diacylamines and ortho-Nosylamide as Ammonia Equivalents", Agnew. Chem. Int. Ed. 2006, pp. 5546-5549, vol. 45.
Andreas Leitner et al., "A Simple Iridium Catalyst with a Single Resolved Stereocenter for Enantioselective Allylic Amination. Catalyst Selection from Mechanistic Analysis", J. Am. Chem. Soc. 2005, pp. 15506-15514, vol. 127, No. 44.
Shashank Shekhar et al., "Sequential Catalytic Isomerization and Allylic Substitution. Conversion of Racemic Branched Allylic Carbonates to Enantioenriched Allylic Substitution Products", J. Am. Chem. Soc. 2006, pp. 11770-11771, vol. 128, No. 36.
Teruyuki Kondo et al., "Nucleophilic and Electrophilic Allylation Reactions. Synthesis, Structure, and Ambiphilic Reactivity of ($\eta^3$-Allylruthenium(II) Complexes", Organometallics 1995, pp. 1945-1953, vol. 14, No. 4.
Mbaye D. Mbaye et al., "[Cp*($\eta^2$-bipy)(MeCN)Ru$^{II}$[PF$_6$] Catalysts for Regioselective Allylic Substitution and Characterization of Dicationic [Cp*($\eta^2$-bipy)-($\eta^3$-allyl)Ru$^{IV}$][PF$_6$]$_2$ Intermediates", Agnew. Chem. Int. Ed. 2003, pp. 5066-5068, vol. 42.
Markus Roggen et al., "Stereospecific Substitution of Allylic Alcohols to Give Optically Active Primary Allylic Amines: Unique Reactivity of a (P,alkene)Ir Complex Modulated by Iodide", J. Am. Chem. Soc. 2010, pp. 11917-11919, vol. 132, No. 34.
Communication dated Apr. 2, 2015 from the European Patent Office in counterpart Application No. 12826973.5.

(Continued)

Primary Examiner — Clinton Brooks
(74) Attorney, Agent, or Firm — Sughrue Mion, PLLC

(57) ABSTRACT

Provided is a method for producing a 2-alkenylamine compound efficiently and at low cost, using a primary or secondary amine compound and a 2-alkenyl compound as the starting materials therefor. The 2-alkenylamine compound is produced by adding Bronsted acid when 2-alkenylating by reacting the primary or secondary amine compound with the 2-alkenyl compound, and 2-alkenylating in the presence of a catalyst comprising a complexing agent and a transition metal precursor stabilized by a monovalent anionic five-membered conjugated diene.

10 Claims, 1 Drawing Sheet

(56) References Cited

OTHER PUBLICATIONS

Hui Jun Zhang et al, "Novel [Ruthenium(Substituted-Tetramethylcyclopentadiene)(2-Quinolinecarboxylato)(Allyl)] Hexafluorophosphate Complexes as Efficient Catalysts for Highly Regioselective Nucleophilic Substitution of Aliphatic Allylic Substrates", Advanced Synthesis & Catalysis, vol. 350, 2008, p. 1601-1609, XP002737028, Wiley-VCH Verlang GmbH, ISSN:1615-4150.

Hui Jun Zhang et al.,"Ruthenium-catalyzed 1-10 Nucleophilic Allylic Substitution Reactions from Beta-Silylated Allylic Carbonates", Organometallics., vol. 28, 2009, pp. 5173-5182, XP002737029, ACS, Washington D.C., ISSN: 0276-7333.

\* cited by examiner

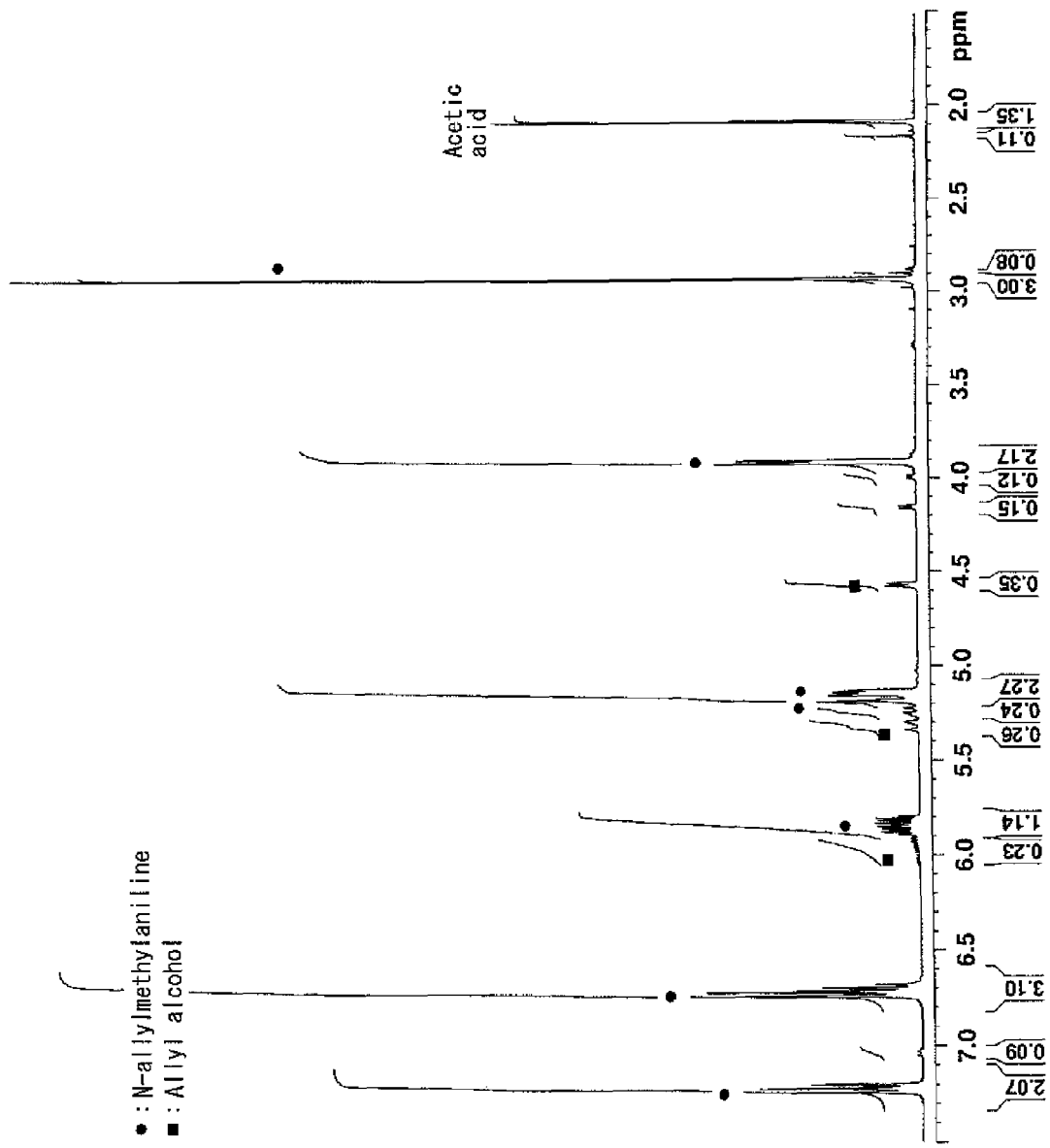

PRODUCTION METHOD FOR 2-ALKENYLAMINE COMPOUND

CROSS REFERENCE TO RELATED APPLICATIONS

This application is a National Stage of International Application No. PCT/JP2012/071855 filed Aug. 29, 2012 (claiming priority based on Japanese Patent Application No. 2011-188545 filed Aug. 31, 2011), the contents of which are incorporated herein by reference in their entirety.

TECHNICAL FIELD

The present invention relates to a method for producing 2-alkenylamine compounds typified by allylamine. More particularly, it relates to a method capable of producing 2-alkenylamine compounds at a high efficiency by reacting an amino group-containing compound with a 2-alkenyl compound in the presence of a specific transition metal complex and a ligand.

BACKGROUND ART

2-Alkenylamine compounds typified by allylamine have an olefin site (carbon-carbon double bond) which can be transformed into a functional group and a hetero atom (nitrogen atom), and provide building blocks useful in organic synthesis. They are therefore widely used as biologically active functional molecules, such as pharmaceuticals and agricultural chemicals, modifiers for polymers, and catalysts for chemical reactions, etc.

As a method for producing allylamines, there is known a method of reacting allyl chloride and ammonia water (Patent Literature 1). In this method, three allyl compounds, such as monoallylamine, diallylamine and triallylamine, are formed, and its side reactions (allylamine byproduct) will reduce the yield of the target product. Since the same stoichiometric amount of a salt as the product is formed, and a halogen compound is used as a raw material, it has a heavy environmental burden. In addition, in this method, an organic chlorine compound inevitably remains in the allyl compound, which produces a drawback of a poor insulating property and thus is unsuitable for use in electronics applications, for example.

In order to solve this problem, in recent years, methods of allylating amines with various transition metal catalysts that employ no halide as the allylating agent have been developed. For example, Non-patent Literature 1 reports an allylation method using a palladium catalyst in which allyl acetate is used as the allylating agent, and N,N-diformylamide is used as the substrate. However, the nucleophilicity of the amine (N,N-diformylamide) is low thereby requiring a strong base for converting into a lithium salt or a sodium salt, and the reactivity of the amine is also low thereby requiring a long time for allylation.

On the other hand, Non-patent Literature 2 describes an asymmetric allylation method using benzylamine as the substrate, and using a catalyst having palladium as the center metal, and a bidentate optically active phosphite-thioether compound as the ligand. While the amount of catalyst is small and its reactivity is high, the method requires as the solvent a halogen-based solvent placing a heavy burden on the environment, the reaction temperature must be maintained at a low level, the ligand must be separately synthesized, and catalyst preparation is cumbersome, thus rendering the industrialization of the method difficult.

Non-patent Literature 3 discloses a method for preparing allylamines using allyl carbonate as the allylating agent and a neutral rhodium complex. With trimethyl phosphite as the ligand, the reaction proceeds at room temperature in a THF solvent. However, since the amine nucleophile must be protected with toluenesulfonic acid and then must be changed to an anion using a superstoichiometric amount of a base, in order to enhance its reactivity, the reaction is essentially carried out under a strongly basic condition. The ligand and amine equivalent anion are vulnerable to oxygen and moisture, and thus the method is not suitable for large-scale synthesis.

As examples of using an iridium catalyst, methods of allylating an amine with an allylating agent, such as allyl carbonate and allyl acetate, are reported in Non-patent Literatures 4 to 6. In the methods, the yields are high, and the allylated target products can be obtained from both aliphatic amines and aromatic amines. When allyl carbonate is used as the allylating agent, decarboxylation and elimination of alcohol, such as methanol, may provide a driving force for the reaction. For large scale industrial production, the formation of gases, such as carbon dioxide, in the coproduct poses a problem in terms of safety. In addition, an expensive iridium and (chiral)phosphoramidite ligand is required as the catalyst, which is disadvantageous costwise, and depending on substrates, a stoichiometric amount of a base, such as triazabicycloundecene (TBD) or triethylamine, is required.

Methods are also known in which ruthenium is used as the center metal. Non-patent Literature 7 discloses an allylation method in which allyl carbonate is used as the allylating agent and a neutral ruthenium complex having a cyclopentadienyl anion as a complexing agent is used as the catalyst. The reaction will be complete in an hour in a THF solvent at 0° C. A highly nucleophilic piperidine is used as the amine. The feasibility of its use in other substrates is unknown.

Non-patent Literature 8 also discloses a method for producing allylamines using a dicationic ruthenium complex. By using a catalyst having a pentamethylcyclopentadienyl anion as the complexing agent, bipyridine as the ligand, and a hexafluorophosphate anion as the counter-cation, the reaction proceeds in a solvent at room temperature. These are pioneering results demonstrating the reactivity of a ruthenium complex to allylation, but in both of the references, the reactivity is low, a large amount of catalyst is required, and an allylating agent of the decarboxylation type is used, and thus it is impossible to avoid the above industrial problems.

Patent Literature 2 and Non-patent Literature 9 disclose a method for producing allylamines from allyl alcohol using a phosphoramidite ligand and an iridium catalyst. Using allyl alcohol as the allylating agent and sulfamic acid as the amine source, a primary branched allylamine can be selectively obtained. It may be mentioned as an example that first indicated a possibility of using allyl alcohol as the allylating agent, but it is accompanied by difficulties in industrialization in terms of catalyst cost and catalyst preparation.

Patent Literature 3 discloses a method for producing allyl ethers in the presence of a cyclopentadienyl ruthenium complex having an α-imino acid type ligand or an α-amino acid type ligand. According to this method, an allyl ether can be produced from an allyl alcohol and an alcohol in a dehydrating manner without using any additives. The coproduct is only water, and thus it is an environmentally friendly and very efficient method, but when applied for amines, the basicity of the substrate is believed to inhibit protonation of a ligand required for catalyst activation resulting in the loss of catalyst performance. Thus, the allylation reaction with a basic compound was thought not to proceed and its application into such a compound has not been put into practice.

CITATION LIST

Patent Literature

[PLT 1] Japanese Unexamined Patent Publication (Kokai) No. 8-283209
[PLT 2] Japanese Unexamined Patent Publication (Kokai) No. 2009-46452
[PLT 3] Japanese Unexamined Patent Publication (Kokai) No. 2005-289977

Non-Patent Literature

[NPL 1] K. Ding et al., J. Org. Chem., 66, pp. 3238-3241 (2001).
[NPL 2] D. A. Evans et al., J. Am. Chem. Soc., 122, pp. 7905-7920 (2000).
[NPL 3] P. A. Evans et al., Org. Lett., 1, pp. 1929-1931 (1999).
[NPL 4] G. Helmchen et al., Angew. Chem. Int. Ed., 45, pp. 5546-5549 (2006).
[NPL 5] J. F. Hartwig et al., J. Am. Chem. Soc., 127, pp. 15506-15514 (2005).
[NPL 6] J. F. Hartwig et al., J. Am. Chem. Soc., 128, pp. 11770-11771 (2006).
[NPL 7] T. Kondo, Y. Watanabe et al., Organometallics, 14, pp. 1945-1953 (1995).
[NPL 8] B. Demerseman, C. Bruneau et al., Angew. Chem. Int. Ed., 42, pp. 5066-5068 (2003).
[NPL 9] E, M. Carreira et al., J. Am. Chem. Soc. 132, pp. 11917-11919 (2010).

SUMMARY OF THE INVENTION

Problems to be Solved by the Invention

It is an object of the present invention to provide a method for producing a 2-alkenylamine compound at a high efficiency using a corresponding amino group-containing compound and a corresponding 2-alkenylating agent as the starting material.

Means to Solve the Problems

After intensive and extensive experiments to solve the above problems, the present inventors have found that a 2-alkenylamine compound can be efficiently obtained by using a Bronsted acid in the 2-alkenylation reaction of an amine compound using a cyclopentadienyl ruthenium complex (transition metal complex) having an α-imino acid type ligand, in which 2-alkenylation reaction it was conventionally believed that the protonation of a ligand required for catalyst activation is inhibited and thus the performance of the catalyst is lost due to the basicity of a substrate (an amine compound), and thereby have completed the present invention.

Thus, the present invention is as shown below:

[1] A method for producing a 2-alkenylamine compound by reacting a primary or secondary amine compound with a 2-alkenyl compound in the presence of a catalyst, wherein the catalyst is a transition metal complex which is a reaction product of a complexing agent having a nitrogen coordination site and an oxygen coordination site bidentate-coordinated to a transition metal atom in the molecule and a transition metal precursor having a monovalent anionic five-membered ring-conjugated diene as a ligand in the molecule, and wherein a Bronsted acid is added.

[2] The method for producing a 2-alkenylamine compound according to the above [1] wherein the complexing agent is an α-imino acid type ligand compound represented by the following formula (2):

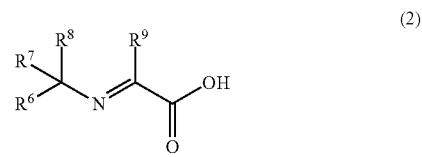

(2)

wherein $R^6$ to $R^9$ represent, independently from each other, a hydrogen atom, a C1 to C10 alkyl group, a C3 to C12 cycloalkyl group, a C6 to C10 aryl group, or an alkyl-substituted silyl group, said substituent having a total of 1 to 30 carbons, or an aryl-substituted silyl group, said substituent having a total of 6 to 30 carbons, or $R^6$ and $R^7$, $R^7$ and $R^8$, $R^8$ and $R^9$, $R^6$ and $R^8$, $R^6$ and $R^9$, or $R^7$ and $R^9$ may bind to each other to form a saturated or unsaturated 4 to 8-membered ring.

[3] The method for producing a 2-alkenylamine compound according to the above [1] or [2], wherein the transition metal precursor comprises at least one of transition metal atoms selected from the group consisting of the transition metals belonging to Group 8 and Group 9 of the periodic table.

[4] The method for producing a 2-alkenylamine compound according to the above [3], wherein the transition metal atom is selected from the group consisting of ruthenium, rhodium, and iridium.

[5] The method for producing a 2-alkenylamine compound according to any one of the above [1] to [4], wherein the monovalent anionic 5-membered ring-conjugated diene has a conjugatable monovalent anionic structure, wherein the anion is conjugated to the binding carbons of $R^{10}$ to $R^{30}$, the structure represented by any of the following formula (3):

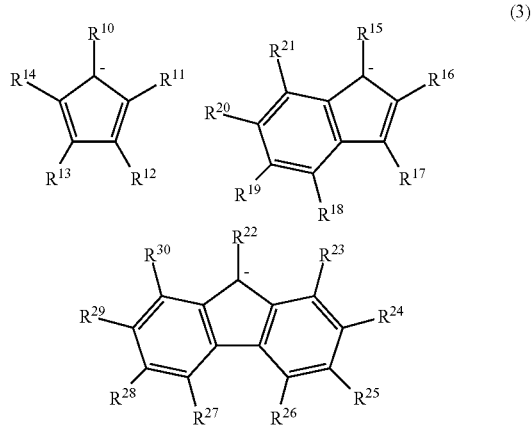

(3)

wherein $R^{10}$ to $R^{30}$ represent, independently from each other, a hydrogen atom, a C1 to C10 alkyl group, a C3 to C12 cycloalkyl group, a C6 to C10 aryl group, or an alkyl-substituted silyl group, said substituent having a total of 1 to 30 carbons, or an aryl-substituted silyl group, said substituent having a total of 6 to 30 carbons, and groups binding to adjacent two carbon atoms on the ring may bind to each other to form a saturated or unsaturated 4 to 8-membered ring together with the adjacent two carbon atoms.

[6] The method for producing a 2-alkenylamine compound according to any one of the above [1] to [5], wherein the 2-alkenyl compound is a compound represented by the following formula (1):

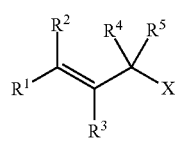

(1)

wherein $R^1$, $R^2$, $R^3$, $R^4$ and $R^5$ represent, independently from each other, a hydrogen atom, a C1 to C10 alkyl group, a C2 to C10 alkenyl group, a C1 to C10 alkoxy group, a C3 to C12 cycloalkyl group, a C3 to C12 cycloalkenyl group, an acetoxy group, or a C6 to C10 aryl group; and X represents a substituent selected from the group consisting of $NO_2$—, HO—, RO—, $RS(O)_2O$—, RCOO—, and ROCOO— wherein R is a C1 to C30 organic group.

[7] The method for producing a 2-alkenylamine compound according to the above [6], wherein all of $R^1$, $R^2$, $R^3$, $R^4$ and $R^5$ in formula (1) each are a hydrogen atom.

[8] The method for producing a 2-alkenylamine compound according to any one of the above [1] to [7], wherein the primary or secondary amine compound is selected from the group consisting of a saturated C1 to C30 aliphatic amine having one or two amino group(s) in the molecule, a saturated C3 to C30 alicyclic amine having one or two amino group(s) in the molecule, a C6 to C30 arylamine compound having 1 to 10 amino group(s) in the molecule, and a nitrogen-containing C2 to C30 heterocyclic compound having a hydrogen atom on the nitrogen atom constituting the heterocyclic ring.

[9] The method for producing a 2-alkenylamine compound according to any one of the above [1] to [8], wherein 0.000001 to 10 moles of the transition metal complex is used relative to one total mole of the primary or secondary amine compound and the 2-alkenyl compound (moles of the primary or secondary amine compound plus moles of the 2-alkenyl compound).

[10] The method for producing a 2-alkenylamine compound according to any one of the above [1] to [9], comprising the steps of:

reacting a compound having a monovalent anionic 5-membered ring-conjugated diene backbone and a transition metal compound to produce a transition metal precursor having a monovalent anionic 5-membered ring-conjugated diene as a ligand in the molecule, mixing the transition metal precursor and a complexing agent to produce a transition metal complex, and mixing and reacting the transition metal complex, a primary or secondary amine compound, a Bronsted acid and a 2-alkenyl compound to produce a 2-alkenylamine compound.

Effects of the Invention

According to the method for producing a 2-alkenylamine compound of the present invention, an additive, such as a strong base that was conventionally required in cases where an allylating agent (2-alkenylating agent), such as allyl acetate, and a salt, such as palladium acetate, were used as the catalyst is not necessary. Since an amine compound becomes a salt when a Bronsted acid is added thereto, there can be provided a method that permits a reaction under mild near-neutral conditions and that is highly productive and environmentally friendly. Depending on the solubility or reactivity of the amine compound, the reaction can proceed without using a solvent. Since the method for producing a 2-alkenylamine compound of the present invention can use abundantly-supplied and inexpensive carboxylic acid allyl esters and allyl alcohols as an allylating agent, which is a representative 2-alkenylating agent, and is highly productive for industrialization, the method is very useful in terms of productivity and handling.

BRIEF DESCRIPTION OF THE DRAWINGS

FIG. 1 A $^1$H-NMR spectrum of a 2-alkenylated (allylated) product obtained in Example 1 of the present invention.

MODE FOR CARRYING OUT THE INVENTION

The present invention will now be explained in detail below.

The method for producing a 2-alkenylamine compound of the present invention comprises adding a Bronsted acid when 2-alkenylating a primary or secondary amine compound by reacting it with a 2-alkenyl compound, and using, as a catalyst, a transition metal complex which is a reaction product of a complexing agent and a transition metal precursor having a monovalent anionic 5-membered ring-conjugated diene as a ligand in the molecule.

The primary or secondary amine compound for use in the present invention may be any compound having one amino group or a compound having two or more amino groups as long as it is a compound having an amino group bearing a hydrogen atom, and may not be specifically limited. As used herein a "primary amine" compound refers to a compound that has a primary amino group but not a secondary amino group (a tertiary amine backbone may be contained in the molecule), and a "secondary amine" compound refers to a compound that has at least one secondary amino group (a primary amino group and/or a tertiary amine backbone may be contained in the molecule).

As a primary or secondary amine compound, there can be mentioned a saturated C1 to C30 aliphatic primary amine having one amino group in the molecule, a saturated C2 to C30 aliphatic secondary amine having one amino group in the molecule, an unsaturated C2 to C30 aliphatic primary amine having one amino group in the molecule, an unsaturated C3 to C30 aliphatic secondary amine having one amino group in the molecule, a saturated or unsaturated C3 to C30 alicyclic primary amine having one amino group in the molecule, a saturated or unsaturated C4 to C30 alicyclic secondary amine having one amino group in the molecule, a saturated C1 to C30 aliphatic primary diamine or polyamine having two or more amino groups in the molecule, a saturated C2 to C30 aliphatic secondary diamine or polyamine having two or more amino groups in the molecule, an unsaturated C2 to C30 aliphatic primary diamine or polyamine having two or more amino groups in the molecule, an unsaturated C3 to C30 aliphatic secondary diamine or polyamine having two or more amino groups in the molecule, a saturated C3 to C30 alicyclic primary diamine or polyamine having two or more amino groups in the molecule, a saturated C4 to C30 alicyclic secondary diamine or polyamine having two or more amino groups in the molecule, an unsaturated C3 to C30 alicyclic primary diamine or polyamine having two or more amino groups in the molecule, an unsaturated C4 to C30 alicyclic secondary diamine or polyamine having two or more amino groups in the molecule, a C6 to C30 mono-primary aminoaryl compound having one amino group in the molecule, a C7 to C30 mono-secondary aminoaryl compound having one amino group in the molecule, a C6 to C30 poly-primary aminoaryl compound having 2 to 10 amino groups in the molecule, a C7 to C30 poly-secondary aminoaryl compound having 2 to 10 amino groups in the molecule, a nitrogen-containing C2 to C30 heterocyclic compound having a hydrogen atom on the nitrogen atom constituting the heterocyclic ring, and the like. The primary or secondary amine compounds may comprise a substituent, such as a halogen atom.

Specific examples of a saturated C1 to C30 aliphatic primary amine having one amino group in the molecule include methylamine, ethylamine, n-propylamine, i-propylamine, n-butylamine, tert-butylamine, neopentyl amine, 2-ethylhexylamine, n-octylamine, and the like. Specific examples of a saturated C2 to C30 aliphatic secondary amine having one amino group in the molecule include dimethylamine, diethylamine, diisopropylamine, dibutylamine, and the like. Specific examples of an unsaturated C2 to C30 aliphatic primary amine having one amino group in the molecule include allylamine, crotylamine, and the like. Specific examples of an unsaturated C3 to C30 aliphatic secondary amine having one amino group in the molecule include diallylamine, and the like. Specific examples of a saturated C3 to C30 alicyclic primary amine having one amino group in the molecule include 2-methylcyclopentylamine, cyclohexylamine, amantadine, and the like. Specific examples of a saturated C4 to C30 alicyclic secondary amine having one amino group in the molecule include N,N-methylcyclopentylamine, N,N-methylcyclohexylamine, and the like. Specific examples of an unsaturated C3 to C30 alicyclic primary amine having one amino group in the molecule include 2-(1-cyclohexenyl)ethylamine, and the like. Specific examples of an unsaturated C4 to C30 alicyclic secondary amine having one amino group in the molecule include N-methyl-2-(1-cyclohexenyl)ethylamine, and the like.

Specific examples of a saturated C1 to C30 aliphatic primary diamine or polyamine having two or more amino groups in the molecule include 1,2-ethanediamine, 1,3-propanediamine, 1,4-butanediamine, 2-chloro-1,3-propanediamine, N,N-dimethylethylenediamine, and the like. Specific examples of a saturated C2 to C30 aliphatic secondary diamine or polyamine having two or more amino groups in the molecule include N,N'-dimethylethylenediamine, N,N'-dimethyl-2-chloro-1,3-propanediamine, N-methylethylenediamine, N,N,N'-trimethylethylenediamine, and the like. Specific examples of an unsaturated C2 to C30 aliphatic primary diamine or polyamine having two or more amino groups in the molecule include 2-butene-1,4-diamine, and the like. Specific examples of an unsaturated C3 to C30 aliphatic secondary diamine or polyamine having two or more amino groups in the molecule include N,N'-dimethyl-2-butene-1,4-diamine, and the like. Specific examples of a saturated C3 to C30 alicyclic primary amine having two or more amino groups in the molecule include 1,2-cyclopentanediamine, (cyclohexane-1,4-diyl)bis(methanamine), and the like. Specific examples of a saturated C4 to C30 alicyclic secondary amine having two or more amino groups in the molecule include N,N'-dimethyl-1,2-cyclopentanediamine, N,N'-dimethyl-(cyclohexane-1,4-diyl)bis(methanamine), and the like. Specific examples of an unsaturated C3 to C30 alicyclic primary amine having two or more amino groups in the molecule include is 1,2-cyclopentenediamine, (1-cyclohexene-1,4-diyl)bis(methanamine), and the like. Specific examples of an unsaturated C4 to C30 alicyclic secondary amine having two or more amino groups in the molecule include N,N'-dimethyl-1,2-cyclopentenediamine, N,N'-dimethyl-(1-cyclohexene-1,4-diyl)bis(methanamine), and the like.

Specific examples of a C6 to C30 mono-primary aminoaryl compound having one amino group in the molecule include aniline, toluidine, 4-nitroaniline, 2,4-di-tert-butylaniline, 2,4-di-tert-butyl-6-methylaniline, 1-aminonaphthalene, 2-aminonaphthalene, benzylamine, 2-phenylethylamine, and the like. Specific examples of a C7 to C30 mono-secondary aminoaryl compound having one amino group in the molecule include N-methylaniline, N-methyltoluidine, and the like. Specific examples of a C6 to C30 poly-primary aminoaryl compound having 2 to 10 amino groups in the molecule include benzidine, 1,2-diaminonaphthalene, 1,8-diaminonaphthalene, 1-methyl-2,3-diaminonaphthalene, 1,2,4-benzenetriamine, and the like. Specific examples of a C7 to C30 poly-secondary aminoaryl compound having 2 to 10 amino groups in the molecule include N,N'-dimethylbenzidine, N,N'-dimethyl-1,2-diaminonaphthalene, N,N'-dimethyl-1,8-diaminonaphthalene, N,N'-dimethyl-1-methyl-2,3-diaminonaphthalene, N,N',N"-trimethyl-1,2,4-benzenetriamine, and the like.

Specific examples of a nitrogen-containing C2 to C30 heterocyclic compound having a hydrogen atom on the nitrogen atom constituting the heterocyclic ring include aziridine, azetidine, pyrrolidine, piperidine, azepane, morpholine, azoles (e.g., pyrazole, imidazole, etc.), imidazoline, thiazine, indole, benzimidazole, and the like.

These primary or secondary amine compounds may preferably be selected from the group consisting of a saturated C1 to C30 aliphatic amine having one or two amino group(s) in the molecule, a saturated C3 to C30 alicyclic amine having one or two amino group(s) in the molecule, a C6 to C30 arylamine compound having 1 to 10 amino groups in the molecule, and a nitrogen-containing C2 to C30 heterocyclic compound having a hydrogen atom on the nitrogen atom constituting the heterocyclic ring.

A 2-alkenyl compound for use in the present invention is not specifically limited as long as it can react with the amino group of a primary or secondary amine compound to form 2-alkenylamine, and include those represented, for example, by the following formula (1). As used herein "2-alkenyl compound" refers to a compound in which a double bond is formed between a carbon atom at the β position adjacent to a carbon atom to which substituent X is bound and a carbon atom located at the adjacent γ position. As a representative example, there can be mentioned an allyl compound in which all of $R^1$, $R^2$, $R^3$, $R^4$ and $R^5$ in formula (1) each are a hydrogen atom. As used herein "2-alkenylamine" refers to an amine compound in which a double bond is formed between a carbon atom at the β position adjacent to a carbon atom to which the nitrogen atom of an amino group is bound and a carbon atom located at the adjacent γ position. As a representative example, there can be mentioned allylamine.

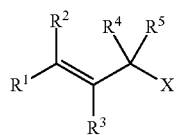

wherein $R^1$, $R^2$, $R^3$, $R^4$ and $R^5$ represent, independently from each other, a hydrogen atom, a C1 to C10 alkyl group, a C2 to C10 alkenyl group, a C1 to C10 alkoxy group, a C3 to C12 cycloalkyl group, a C3 to C12 cycloalkenyl group, an acetoxy group, or a C6 to C10 aryl group; and X represents a substituent selected from the group consisting of $NO_2$—, HO—, RO—, $RS(O)_2O$—, RCOO—, and ROCOO— wherein R is a C1 to C30 organic group. $R^1$, $R^2$, $R^3$, $R^4$ and $R^5$ may preferably be a hydrogen atom, a C1 to C10 alkyl group or a C2 to C10 alkenyl group, and R may preferably be a C1 to C10 alkyl group or a C6 to C10 aryl group.

Specific examples of a 2-alkenyl compound in which X is $NO_2$— include 1-nitro-2-butene, 1-nitro-1,3-diphenyl-2-propene, 3-nitro-3-methoxypropene, and the like. Specific examples of a 2-alkenyl compound in which X is HO— include allyl alcohol, 2-buten-1-ol, 2-methylpropen-1-ol, 3-buten-2-ol, and the like. Specific examples of a 2-alkenyl compound in which X is RO— include methyl allylether, ethyl allylether, diallylether, allyl phenylether, and the like. Specific examples of a 2-alkenyl compound in which X is $RS(O)_2O$— include allyl benzenesulfonate, allyl p-toluenesulfonate, and the like. Specific examples of a 2-alkenyl compound in which X is RCOO— include allyl acetate, 2-hexenyl acetate, 2,4-hexadienyl acetate, prenyl acetate, geranyl acetate, farnesyl acetate, cinnamyl acetate, linalyl acetate, 3-buten-2-yl acetate, 2-cyclopentenyl acetate, 2-trimethylsilylmethyl-2-propenyl acetate, 2-methyl-2-cyclohexenyl acetate, 1-phenyl-1-buten-3-yl propionate, 1-cyclohexyl-2-butene butyrate, 4-cyclopentene-1,3-diol-1-acetate, 1,4-diacetoxybutene-2,3-acetoxy-4-hydroxybutene-1, and the like. Specific examples of a 2-alkenyl compound in which X is ROCOO— include allyl methyl carbonate ester, 4-acetoxy-2-butenyl ethyl carbonate ester, neryl methyl carbonate ester, diallyl carbonate, and the like. These 2-alkenyl compounds may be used alone or a plurality of them may be used in combination as appropriate. The most preferred 2-alkenyl compound for use in the present invention is a carboxylic acid ester in which X is RCOO— and a carbonate ester in which X is ROCOO—, since their elimination products are highly stable and they are easily available.

The amount used of a 2-alkenyl compound relative to a primary or secondary amine compound may be 0.1 to 500 equivalents of the 2-alkenyl compound per equivalent of the hydrogen atoms on the amino groups of the primary or secondary amine compound, preferably 0.5 to 50 equivalents, and more preferably 1 to 20 equivalents. When the equivalent of the 2-alkenyl compound per equivalent of the hydrogen atoms on the amino groups of a primary or secondary amine compound is significantly greater than 1 (the equivalent ratio of 1), the excess 2-alkenyl compound can be used not only as a 2-alkenylating agent but also as a solvent. When the equivalent of the 2-alkenyl compound per equivalent of the hydrogen atoms on the amino groups of a primary or secondary amine compound is less than 1 (the equivalent ratio of 1), the rate of conversion into the target product may become extremely low, which becomes pronounced when the equivalent ratio is less than 0.1. When the equivalent ratio is less than 1, the excess primary or secondary amine compound may be recovered, as needed, and recycled to the process. Since the 2-alkenylation reaction may preferably be carried out in a homogeneous system, a primary or secondary amine compound and a 2-alkenyl compound that can be mixed to a homogeneous liquid form may preferably be used in combination.

Specific examples of a Bronsted acid for use in the present invention include, for example, halogenated hydrogens, such as hydrochloric acid, hydrogen fluoride, hydrogen bromide, and hydrogen iodide, sulfuric acid, sulfonic acids, such as methanesulfonic acid, p-toluenesulfonic acid and trifluoromethane sulfonic acid, oxo acids of phosphorus, such as phosphoric acid, pyrophosphoric acid, polyphosphoric acid, phosphorous acid and hypophosphorous acid, carboxylic acids, such as acetic acid, trifluoroacetic acid and benzoic acid, and boric acids, such as boric acid and phenylboric acid.

The above Bronsted acid may be used at an amount of 0.1 to 500 moles, preferably 0.5 to 50 moles, and more preferably 1 to 20 moles per mole of a primary or secondary amine compound.

The 2-alkenylation reaction may preferably be carried out under near-neutral conditions, and the above Bronsted acid which is a proton source may preferably be reacted in advance with the primary or secondary amine compound to form a salt, which is then be used in the 2-alkenylation reaction.

The transition metal complex for use in the present invention is a complex obtained by the reaction of a complexing agent described below and a transition metal precursor obtained by complex formation of a transition metal compound and a monovalent anionic five-membered ring-conjugated diene compound.

A complexing agent useful in forming a transition metal complex for use in the present invention has a nitrogen coordination site and an oxygen coordination site (a nitrogen atom and an oxygen atom) bidentate-coordinated to a transition metal atom in the molecule, and may preferably be an α-imino acid type ligand compound represented by the following formula (2):

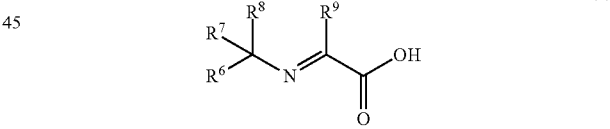

wherein $R^6$ to $R^9$ represent, independently from each other, a hydrogen atom, a C1 to C10 alkyl group, a C3 to C12 cycloalkyl group, a C6 to C10 aryl group, or an alkyl-substituted silyl group, said substituent having a total of 1 to 30 carbons, or an aryl-substituted silyl group, said substituent having a total of 6 to 30 carbons, or $R^6$ and $R^7$, $R^7$ and $R^8$, $R^8$ and $R^9$, $R^6$ and $R^8$, $R^6$ and $R^9$, or $R^7$ and $R^9$ may bind to each other to form a saturated or unsaturated 4 to 8-membered ring. Specific examples of an α-imino acid type ligand compound include, but not limited to, quinaldic acid and picolinic acid. Since an α-imino acid type ligand compound has a high activity toward the 2-alkenylation reaction, it can be preferably used in the present invention. They may be used alone or in combination as appropriate.

As a transition metal compound for use in the production of transition metal precursors useful in the formation of transition metal complexes for use in the present invention, there can be used a compound containing at least one of transition metal atoms selected from the group consisting of transition metals belonging to Group 8 and Group 9 of the periodic table. Specifically, there can be mentioned iron compounds, such as ferric chloride (III), ferric bromide (III) and ferric nitrate (III), ruthenium compounds, such as ruthenium chloride (III), ruthenium bromide (III), ruthenium nitrate (III), hexaamine ruthenium (II) and hexaaqua ruthenium (III), osmium compounds, such as osmium chloride (III) and osmium oxide (VI), cobalt compounds, such as cobalt chloride (III), rhodium compounds, such as rhodium chloride (III), iridium compounds, such as iridium chloride (III) and iridium acetate (II), and the like. Among them, ruthenium compounds, rhodium compounds, and iridium compounds may be preferred, and specifically ruthenium compounds may be preferred, since they have a high activity in the 2-alkenylation reaction and are relatively inexpensive.

According to the present invention, the monovalent anionic five-membered ring-conjugated diene compound reacts with the above transition metal compound thereby to form a transition metal precursor having a stabilized transition metal atom. As used herein, the monovalent anionic five-membered ring-conjugated diene compound refers to a monovalent anion having a cyclopentadienyl backbone in the molecule, and may preferably be a compound having a conjugatable monovalent anionic structure represented by the following formula (3):

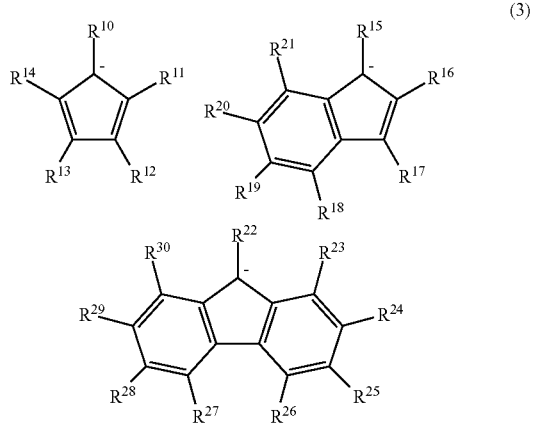

(3)

wherein $R^{10}$ to $R^{30}$ represent, independently from each other, a hydrogen atom, a C1 to C10 alkyl group, a C3 to C12 cycloalkyl group, a C6 to C10 aryl group, or an alkyl-substituted silyl group, said substituent having a total of 1 to 30 carbons, or an aryl-substituted silyl group, said substituent having a total of 6 to 30 carbons, and groups binding to adjacent two carbon atoms on the ring may bind to each other to form a saturated or unsaturated 4 to 8-membered ring together with the adjacent two carbon atoms. Anions are conjugated with the binding carbons of $R^{10}$ to $R^{30}$.

Specific examples of a monovalent anionic five-membered ring-conjugated diene useful in the present invention include, for example, a $\eta^5$-cyclopentadienyl anion, a $\eta^5$-methylcyclopentadienyl anion, a $\eta^5$-dimethylcyclopentadienyl anion, a $\eta^5$-trimethylcyclopentadienyl anion, a $\eta^5$-tetramethylcyclopentadienyl anion, a $\eta^5$-pentamethylcyclopentadienyl anion, a $\eta^5$-ethylcyclopentadienyl anion, a $\eta^5$-n-propylcyclopentadienyl anion, a $\eta^5$-isopropylcyclopentadienyl anion, a $\eta^5$-n-butylcyclopentadienyl anion, a $\eta^5$-sec-butylcyclopentadienyl anion, a $\eta^5$-tert-butylcyclopentadienyl anion, a $\eta^5$-n-pentylcyclopentadienyl anion, a $\eta^5$-neopentylcyclopentadienyl anion, a $\eta^5$-n-hexylcyclopentadienyl anion, a $\eta^5$-n-octylcyclopentadienyl anion, a $\eta^5$-phenylcyclopentadienyl anion, a $\eta^5$-naphthylcyclopentadienyl anion, a $\eta^5$-trimethylsilylcyclopentadienyl anion, a $\eta^5$-triethylsilylcyclopentadienyl anion, a $\eta^5$-tert-butyldimethylsilylcyclopentadienyl anion, a $\eta^5$-indenyl anion, a $\eta^5$-methylindenyl anion, a $\eta^5$-dimethylindenyl anion, a $\eta^5$-ethylindenyl anion, a $\eta^5$-n-propylindenyl anion, a $\eta^5$-isopropylindenyl anion, a $\eta^5$-n-butylindenyl anion, a $\eta^5$-sec-butylindenyl anion, a $\eta^5$-tert-butylindenyl anion, a $\eta^5$-n-pentylindenyl anion, a $\eta^5$-neopentylindenyl anion, a $\eta^5$-n-hexylindenyl anion, a $\eta^5$-n-octylindenyl anion, a $\eta^5$-n-decylindenyl anion, a $\eta^5$-phenylindenyl anion, a $\eta^5$-methylphenylindenyl anion, a $\eta^5$-naphthylindenyl anion, a $\eta^5$-trimethylsilylindenyl anion, a $\eta^5$-triethylsilylindenyl anion, a $\eta^5$-tert-butyldimethylsilylindenyl anion, a $\eta^5$-tetrahydroindenyl anion, a $\eta^5$-fluorenyl anion, a $\eta^5$-methylfluorenyl anion, a $\eta^5$-dimethylfluorenyl anion, a $\eta^5$-ethylfluorenyl anion, a $\eta^5$-diethylfluorenyl anion, a $\eta^5$-n-propylfluorenyl anion, a $\eta^5$-di-n-propylfluorenyl anion, a $\eta^5$-isopropylfluorenyl anion, a $\eta^5$-diisopropylfluorenyl anion, a $\eta^5$-n-butylfluorenyl anion, a $\eta^5$-sec-butylfluorenyl anion, a $\eta^5$-tert-butylfluorenyl anion, a $\eta^5$-di-n-butylfluorenyl anion, a $\eta^5$-di-sec-butylfluorenyl anion, a $\eta^5$-di-tert-butylfluorenyl anion, a $\eta^5$-n-pentylfluorenyl anion, a $\eta^5$-neopentylfluorenyl anion, a $\eta^5$-n-hexylfluorenyl anion, a $\eta^5$-n-octylfluorenyl anion, a $\eta^5$-n-decylfluorenyl anion, a $\eta^5$-n-dodecylfluorenyl anion, a $\eta^5$-phenylfluorenyl anion, a $\eta^5$-di-phenylfluorenyl anion, a $\eta^5$-methylphenylfluorenyl anion, a $\eta^5$-naphthylfluorenyl anion, a $\eta^5$-trimethylsilylfluorenyl anion, a $\eta^5$-bis-trimethylsilylfluorenyl anion, a $\eta^5$-triethylsilylfluorenyl anion, a $\eta^5$-tert-butyldimethylsilylfluorenyl anion and the like, with a $\eta^5$-cyclopentadienyl anion, a $\eta^5$-tetramethyl-cyclopentadienyl anion, a $\eta^5$-pentamethyl-cyclopentadienyl anion, a $\eta^5$-indenyl anion, or a $\eta^5$-fluorenyl anion being preferred. As sources for these monovalent anionic five-membered ring-conjugated dienes, there can be used, for example, compounds having potassium, sodium, lithium, etc., as a counter ion (counter-cation).

The above transition metal precursor may be synthesized by a known method, and preferably be obtained by reacting the above monovalent anionic five-membered ring-conjugated diene compound with a transition metal halide. Suitable methods of preparation are described in, for example, Adv. Synth. Catal., 346, pp. 901-904 (2004) and Japanese PCT Patent Publication (Kohyo) No. 2003-507387. For example, ruthenium chloride (III) and sodium $\eta^5$-cyclopentadienyl may be reacted to obtain a di($\eta^5$-cyclopentadienyl) ruthenium complex, which may then be converted to a cyclopentadienyl ruthenium triacetonitrile complex (transition metal precursor) by the method described in Adv. Synth. Catal., 346, pp. 901-904 (2004).

By dissolving and reacting the above complexing agent and the transition metal precursor in a reaction solvent, a catalyst comprising a transition metal complex can be obtained. The transition metal complex can be obtained by mixing a complexing agent and a transition metal precursor at a mixing ratio (complexing agent/transition metal precursor (molar ratio)) of 0.8 to 1.5, more preferably 0.9 to 1.1, at a reaction temperature of 0 to 100° C., more preferably 20 to 50° C. After dissolving and mixing, both of them react quickly to form a transition metal complex, which thus can be used immediately after dissolving and mixing in a solvent. The complex can also be used after aging for a certain period of time. The reaction time may preferably be 0.01 to 10 hours, more preferably 0.2 to 1 hour.

The 2-alkenylation reaction may preferably be carried out in a homogeneous system, and the transition metal complex may also be preferred to be dissolved in a primary or secondary amine compound and a 2-alkenyl compound. When a transition metal complex is dissolved in a primary or secondary amine compound and a 2-alkenyl compound, the transition metal complex, the primary or secondary amine compound and the 2-alkenyl compound can be simultaneously fed into a reaction vessel and used. The amount used of a catalyst may be controlled as appropriate depending on a variety of factors, such as the form of the catalyst, the type of the reaction (a batch reaction, a continuous fixed bed reaction, a continuous fluidized bed reaction), the amount used of a solvent described below, etc. In general, the amount used of a transition metal complex, when used as a homogeneous system catalyst (the catalyst is dissolved in a reaction system), is 0.000001 to 10 moles per total mole of the primary or secondary amine compound and the 2-alkenyl compound (moles of the primary or secondary amine compound plus moles of the 2-alkenyl compound), and in a batch reaction, 0.000001 to 0.5 moles per total mole of the primary or secondary amine compound and the 2-alkenyl compound. Alternatively, a complexing agent bound to a support (polystyrene, etc.), and a transition metal precursor may be reacted and used as a supported catalyst (a non-homogeneous system catalyst). In a continuous fixed bed or fluidized bed reaction employing such a supported catalyst, the amount used of the transition metal complex is 0.0001 to 0.5 moles per total mole of the primary or secondary amine compound and the 2-alkenyl compound.

For the purpose of homogenization, viscosity adjustment, etc., of a reaction solution in a reaction process, a solvent may be used as needed. As solvents that can be used, there can be mentioned water, aliphatic and aromatic hydrocarbons, aliphatic, alicyclic and aromatic halogenated hydrocarbons, nitro alkanes, and oxygen-containing hydrocarbons, such as ethers, glycol ethers, esters, and ketones. Preferred solvents among them are hexane and octane as examples of aliphatic hydrocarbons, cyclohexane as an example of alicyclic hydrocarbons, toluene and xylene as examples of aromatic hydrocarbons, dichloromethane and 1,2-dichloroethane as examples of aliphatic halogenated hydrocarbons, chlorobenzene as an example of aromatic halogenated hydrocarbons, nitromethane as an example of nitroalkanes, tetrahydrofuran as an example of ethers, dimethoxyethane as an example of glycolethers, ethyl acetate as an example of esters, acetone and methyl ethyl ketone as examples of ketones. In particular, preferred solvents in terms of reactivity, solubility, cost, etc., are cyclohexane, dichloromethane, toluene and dimethoxyethane. These solvents may be used alone or in combination as appropriate.

The above solvent may be used in an amount of not greater than 1,000 parts by mass, preferably 0.5 to 500 parts by mass, and more preferably 1 to 100 parts by mass relative to 100 parts by mass of a primary or secondary amine compound.

The 2-alkenylation reaction may be carried out at a temperature of 10 to 200° C., preferably 50 to 150° C., and more preferably 60 to 90° C. for a period of time sufficient to substantially complete the reaction, usually 0.1 to 72 hours, preferably 0.1 to 48 hours, and more preferably 0.1 to 24 hours. The optimum temperature and time of the 2-alkenylation reaction for each primary or secondary amine compound may vary depending on the reactivity of the primary or secondary amine compound used, the solvent and the catalyst. The reaction may preferably be carried out in a liquid phase, and thus may preferably be carried out under a pressure atmosphere in which the reaction system can be maintained at a liquid phase. For example, a pressure of about 5 to about 2,000 kPa can be used.

After the 2-alkenylation reaction has been carried out until the desired conversion rate can be obtained in the above process, unnecessary components may preferably be removed from the reaction solution using an appropriate method or means. When a homogeneous system catalyst is used, for example, the homogeneous system catalyst and the excess complexing agent used in the synthesis thereof and reaction byproducts remain in the reaction mixture as a homogeneous phase, and these impurities can be separated by washing the reaction solution or treating it with an adsorbing agent. In order to remove the above unnecessary components from the reaction solution, a solvent may preferably be added prior to a post-treatment. By adding a solvent, the viscosity of the reaction solution containing the 2-alkenylation reaction products can be reduced, resulting in the enhanced removal efficiency. The solvent to be added may preferably contain at least one organic solvent selected from the group consisting of an aliphatic, alicyclic and aromatic hydrocarbon, an aliphatic, alicyclic and aromatic halogenated hydrocarbon, a nitroalkane, and an oxygen-containing hydrocarbon, such as an ether, a glycol ether, an ester, and a ketone. Specifically, there can be mentioned at least one organic solvent selected from the group consisting of an aliphatic hydrocarbon, such as hexane and octane, an alicyclic hydrocarbon, such as cyclohexane, an aromatic hydrocarbon, such as toluene and xylene, an aliphatic halogenated hydrocarbon, such as dichloromethane and 1,2-dichloroethane, an aromatic halogenated hydrocarbon, such as chlorobenzene, a nitroalkane, such as nitromethane, an ether, such as tetrahydrofuran, a glycolether, such as dimethoxyethane, an ester, such as ethyl acetate, and a ketone, such as acetone and methyl ethyl ketone. When an elimination product derived from X in formula (1) is soluble in water, water may preferably be added simultaneously to enhance extraction efficiency during washing. In this case, however, a water-insoluble organic solvent needs to be used. The reaction solution separates into an organic layer containing a 2-alkenylamine product, and an aqueous layer containing a 2-alkenylamine salt with a Bronsted acid, a catalyst-derived inorganic salt and a water-soluble elimination product. For the purpose of enhancing the recovery efficiency of the 2-alkenylamine salt with a Bronsted acid contained in the aqueous layer, a basic compound may be added to the aqueous layer to make the pH of the aqueous solution alkaline, i.e., pH greater than 7, so as to enhance the extraction efficiency of the 2-alkenylamine into the organic layer. The aqueous layer, after having been made alkaline, can be separated and removed to discard the unnecessary impurities. By adding a strong base, such as sodium hydroxide, together with the addition of water, the transfer of catalyst residues into the aqueous layer can be promoted.

After separating the homogeneous system catalyst from the 2-alkenylation reaction solution as described above, the separated residues (the separated aqueous layer) are washed again with the same solvent as the added solvent, and the 2-alkenylamine product contained in a trace amount in the aqueous layer is extracted into the washing solution, and by mixing the washing solution with the reaction solution, the recovery rate of the product can be enhanced. By using washing, fractional distillation, extraction distillation, liquid-liquid extraction, solid-liquid extraction, crystallization, or any combinations thereof, the 2-alkenylation reaction product can be separated and recovered from the reaction solution. By way of example, as a method for separating a product when a carboxylic acid allyl ester is used as the 2-alkenylating (allylating) agent, volatile components, such as solvents and unreacted 2-alkenylating (allylating) agent, are removed by distillation or evaporation, and then carboxylic acid byproducts are recovered by distillation or extraction to recover the 2-alkenyl derivative target product as a product at the bottom.

EXAMPLES

The present invention will now be explained in detail with reference to specific examples, but the present invention is not limited thereto in any way.

Example 1

To a 10 mL Schlenk flask with a Young cock, under a stream of argon, quinaldic acid (3.5 mg, 0.02 mmol; manufactured by Tokyo Chemical Industry Co., Ltd.) as a complexing agent and [CpRu(CH$_3$CN)$_3$]PF$_6$ (8.7 mg, 0.02 mmol; manufactured by Aldrich) (Cp: cyclopentadienyl complex) as a transition metal precursor were added. A mixture of N-methylaniline (1.07 g, 10 mmol), allyl alcohol (1.7 g, 30 mmol) (all of $R^1$, $R^2$, $R^3$, $R^4$ and $R^5$ in formula (1) each are a hydrogen atom, and X is HO—) and acetic acid (600 mg, 10 mmol), which had been treated over freeze-dry cycle for three times, was added thereto, and quinaldic acid and [CpRu(CH$_3$CN)$_3$]PF$_6$ were dissolved thereinto, mixed, and agitated at 80° C. for 3 hours. Based on the result of NMR analysis, the 2-alkenylated product (allylated product) of N-methylaniline was obtained at a yield of 95% (the conversion rate of N-methylaniline >99%; the yield of the 2-alkenylated product >95%). Unless otherwise specified, the yield of the 2-alkenylation reaction was determined by $^1$H-NMR spectrum determination under the following conditions for other Examples and Comparative Examples as well.

Conditions for $^1$H-NMR Spectrum Determination:
BRUKER AVANCE400 (manufactured by BRUKER)
Solvent: Deuterochloroform, measuring temperature: 27° C.

Example 2

Except that the complexing agent in Example 1 was changed to picolinic acid (2.4 mg, 0.02 mmol; manufactured by Kanto Chemical Co., Inc.), 2-alkenylation was carried out under exactly the same conditions as in Example 1. Analysis of the solution after the reaction demonstrated that a 2-alkenylated product (allylated product) was obtained with a conversion rate of 93.2% and a yield of 58%. The use of quinaldic acid rather than picolinic acid as the ligand affords a higher yield of the 2-alkenylated product (allylated product).

Example 3

Except that N-methylaniline in Example 1 was changed to 2-phenylethylamine (1.21 g, 10 mmol; manufactured by Tokyo Chemical Industry Co., Ltd.), 2-alkenylation was carried out under exactly the same conditions as in Example 1. Analysis of the solution after the reaction demonstrated that the di(2-alkenylated) product (diallylated product) of 2-phenylethylamine was obtained at a yield of 55.8% and the mono(2-alkenylated) product (monoallylated product) of 2-phenylethylamine was obtained at a yield of 21.2% (the conversion rate of 2-phenylethylamine: 77%).

Example 4

Except that allyl alcohol in Example 1, which is a 2-alkenylating agent, was changed to allyl acetate (3.0 g, 30 mmol; manufactured by Showa Denko Co., Ltd.) (all of $R^1$, $R^2$, $R^3$, $R^4$ and $R^5$ in formula (1) each are a hydrogen atom, and X is CH$_3$COO—), 2-alkenylation was carried out under exactly the same conditions as in Example 1. Analysis of the solution after the reaction demonstrated that a 2-alkenylated product (allylated product) was obtained with a conversion rate of N-methylaniline of 93.2% and a yield of 78%.

Example 5

Except that the catalyst precursor in Example 1 was changed to [Cp*Ru(CH$_3$CN)$_3$]PF$_6$ (10.1 mg, 0.02 mmol; manufactured by Aldrich) (Cp*: pentamethylcyclopentadienyl complex), 2-alkenylation was carried out under exactly the same conditions as in Example 1. Analysis of the solution after the reaction demonstrated that a 2-alkenylated product (allylated product) was obtained with a conversion rate of N-methylaniline of 99.7% and a yield of 76.9%).

Examples 6 to 8

Except that each (2.0 mL) of the solvents described in the following Table 1 coexisted, 2-alkenylation was carried out under the same conditions as in Example 1. The results of analysis of the solutions after the reactions are summarized in Table 1.

TABLE 1

2-Alkenylation when the solvent is present

| Ex. | Solvent | Volume (mL) | Conversion rate (%) | Yield of 2-alkenylated product (%) |
|---|---|---|---|---|
| 6 | Toluene | 2.0 | 91.9 | 75.0 |
| 7 | Cyclohexane | 2.0 | 92.9 | 74.6 |
| 8 | Dimethoxyethane | 2.0 | 95.0 | 83.6 |

Examples 9 to 12

Except that acetic acid used as the Bronsted acid in Example 1 was changed to the Bronsted acids described in the following Table 2, 2-alkenylation was carried out under exactly the same conditions as in Example 1. Table 2 summarizes the results in the order of the Bronsted acid, the amount of substance (mg), moles (mmol), the conversion rate of N-methylaniline (%), and the yield of the 2-alkenylated product (%).

TABLE 2

2-Alkenylation using Bronsted acids different from acetic acid

| Ex. | Bronsted acid | Amount of substance (g) | Moles (mmol) | Time (h) | Conversion rate (%) | Yield of 2-alkenylated product (%) |
|---|---|---|---|---|---|---|
| 9 | 35% Hydrochloric acid | 1.0 | 10 | 1 | 90.6 | 67.9 |
| 10 | 88% Phosphoric acid | 1.2 | 10 | 1 | 94.1 | 88.5 |

TABLE 2-continued

2-Alkenylation using Bronsted acids different from acetic acid

| Ex. | Bronsted acid | Amount of substance (g) | Moles (mmol) | Time (h) | Conversion rate (%) | Yield of 2-alkenylated product (%) |
|---|---|---|---|---|---|---|
| 11 | Boric acid | 0.62 | 10 | 3 | >99 | 87.0 |
| 12 | p-Toluenesulfonic acid | 1.9 | 10 | 3 | >99 | 83.4 |

Comparative Examples 1 to 2

Results obtained by using complexing agents different from the α-imino acid type ligand compound:

Except that quinaldic acid used as the complexing agent in Example 1 was changed to the complexing agents described in the following Table 3, 2-alkenylation was carried out under exactly the same conditions as in Example 1. Table 3 summarizes the results in the order of the complexing agent, the amount of substance (mg), moles (mmol), the conversion rate of N-methylaniline (%), and the yield of the 2-alkenylated product (%).

TABLE 3

2-Alkenylation using complexing agents different from the α-imino acid type ligand compound

| Comp. Ex. | Complexing agent | Amount of substance (mg) | Moles (mmol) | Conversion rate (%) | Yield of 2-alkenylated product (%) |
|---|---|---|---|---|---|
| 1 | Triphenyl-phosphine | 5.2 | 0.02 | 91.4 | 13.4 |
| 2 | p-Toluene-sulfonic acid | 3.8 | 0.02 | 93.9 | 35.1 |

It is believed that when a phosphorus-based ligand, triphenylphosphine, and a sulfonic acid-based ligand, p-toluenesulfonic acid, were used, the yield of the 2-alkenylated product was low and the side reaction (acetylation reaction) is expected to prevail as the main reaction.

Comparative Example 3

Except that the transition metal precursor in Example 1 was changed to palladium acetate (4.4 mg, 0.02 mmol), 2-alkenylation was carried out under exactly the same conditions as in Example 1. Analysis of the solution after the reaction demonstrated that the 2-alkenylation reaction proceeded very little with a conversion rate of <1% and a yield of a 2-alkenylated product of <1%, and no target products were obtained.

Comparative Example 4

Without adding a Bronsted acid in Example 1, 2-alkenylation was carried out under the same conditions as in Example 1. Analysis of the solution after the reaction demonstrated that the 2-alkenylation reaction proceeded very little with a conversion rate of <1% and a yield of the 2-alkenylated product of <1%, and no target products were obtained.

INDUSTRIAL APPLICABILITY

According to the method for producing a 2-alkenylamine compound of the present invention, a 2-alkenylamine can be produced at a high reaction rate by adding a Bronsted acid to the 2-alkenylation reaction system and by selectively 2-alkenylating a primary or secondary amino group with a 2-alkenylating agent. The method can preferably use abundantly-supplied and inexpensive carboxylic acid allyl esters and allyl alcohols as an allylating agent, which is a representative 2-alkenylating agent. Since the method for producing a 2-alkenylamine compound of the present invention is highly productive for industrialization, this is very useful in terms of productivity and handling.

The invention claimed is:

1. A method for producing a 2-alkenylamine compound by reacting a primary or secondary amine compound with a 2-alkenyl compound in the presence of a catalyst, wherein the catalyst is a transition metal complex which is a reaction product of a complexing agent having a nitrogen coordination site and an oxygen coordination site bidentate-coordinated to a transition metal atom in the molecule and a transition metal precursor having a monovalent anionic five-membered ring-conjugated diene as a ligand in the molecule, and wherein a Bronsted acid selected from the group consisting of halogenated hydrogens, sulfuric acid, sulfonic acids, oxo acids of phosphorus, carboxylic acids, and boric acids is added, wherein the complexing agent is an α-imino acid type ligand compound of the following formula (2):

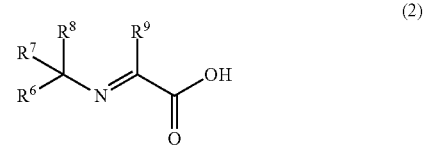

(2)

wherein $R^6$ to $R^9$ are, independently from each other, a hydrogen atom, a C1 to C10 alkyl group, a C3 to C12 cycloalkyl group, a C6 to C10 aryl group, an alkyl-substituted silyl group, said substituent having a total of 1 to 30 carbons, or an aryl-substituted silyl group, said substituent having a total of 6 to 30 carbons, or $R^6$ and $R^7$, $R^7$ and $R^8$, $R^8$ and $R^9$, $R^6$ and $R^8$, $R^6$ and $R^9$, or $R^7$ and $R^9$ may bind to each other to form a saturated or unsaturated 4 to 8-membered ring, wherein the monovalent anionic 5-membered ring-conjugated diene has a conjugatable monovalent anionic structure, wherein the anion is conjugated to the binding carbons of $R^{10}$ to $R^{30}$, the structure of any of the following formulae (3-1), (3-2) and (3-3):

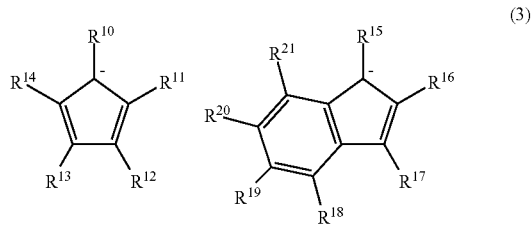

(3)

-continued

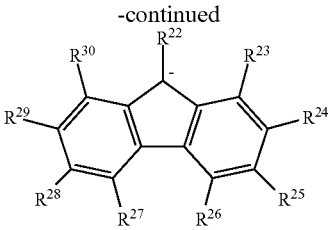

wherein $R^{10}$ to $R^{30}$ are, independently from each other, a hydrogen atom, a C1 to C10 alkyl group, a C3 to C12 cycloalkyl group, a C6 to C10 aryl group, an alkyl-substituted silyl group, said substituent having a total of 1 to 30 carbons, or an aryl-substituted silyl group, said substituent having a total of 6 to 30 carbons, and groups binding to adjacent two carbon atoms on the ring may bind to each other to form a saturated or unsaturated 4 to 8-membered ring together with the adjacent two carbon atoms, wherein the 2-alkenyl compound is a compound of the following formula (1):

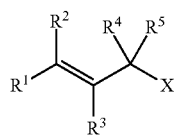

(1)

wherein $R^1$, $R^2$, $R^3$, $R^4$ and $R^5$ are, independently from each other, a hydrogen atom, a C1 to C10 alkyl group, a C2 to C10 alkenyl group, a C1 to C10 alkoxy group, a C3 to C12 cycloalkyl group, a C3 to C12 cycloalkenyl group, an acetoxy group, or a C6 to C10 aryl group; and X is a substituent selected from the group consisting of —NO₂, HO—, RO—, RS(O)₂O—, RCOO—, and ROCOO— wherein R is a C1 to C30 organic group, and wherein the Bronsted acid is used at an amount of 1 to 20 moles per mole of the primary or secondary amine compound.

2. The method for producing a 2-alkenylamine compound according to claim 1, wherein the transition metal precursor comprises at least one of transition metal atoms selected from the group consisting of the transition metals belonging to Group 8 and Group 9 of the periodic table.

3. The method for producing a 2-alkenylamine compound according to claim 2, wherein the transition metal atom is selected from the group consisting of ruthenium, rhodium, and iridium.

4. The method for producing a 2-alkenylamine compound according to claim 1, wherein all of $R^1$, $R^2$, $R^3$, $R^4$ and $R^5$ in formula (1) each are a hydrogen atom.

5. The method for producing a 2-alkenylamine compound according to claim 1, wherein the primary or secondary amine compound is selected from the group consisting of a saturated C1 to C30 aliphatic amine having one or two amino group(s) in the molecule, a saturated C3 to C30 alicyclic amine having one or two amino group(s) in the molecule, a C6 to C30 arylamine compound having 1 to 10 amino group(s) in the molecule, and a nitrogen-containing C2 to C30 heterocyclic compound having a hydrogen atom on the nitrogen atom constituting the heterocyclic ring.

6. The method for producing a 2-alkenylamine compound according to claim 1, wherein 0.000001 to 10 moles of the transition metal complex is used relative to one total mole of the primary or secondary amine compound and the 2-alkenyl compound (moles of the primary or secondary amine compound plus moles of the 2-alkenyl compound).

7. The method for producing a 2-alkenylamine compound according to claim 1, comprising the steps of:
reacting a compound having a monovalent anionic 5-membered ring-conjugated diene backbone and a transition metal compound to produce the transition metal precursor having the monovalent anionic 5-membered ring-conjugated diene as a ligand in the molecule,
mixing the transition metal precursor and the complexing agent to produce the transition metal complex, and
mixing and reacting the transition metal complex, the primary or secondary amine compound, the Bronsted acid and the 2-alkenyl compound to produce a 2-alkenylamine compound.

8. The method for producing a 2-alkenylamine compound according to claim 1, wherein $R^{10}$ to $R^{30}$ are a hydrogen atom.

9. The method for producing a 2-alkenylamine compound according to claim 8, the conjugatable monovalent anionic structure is of the formula:

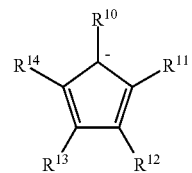

(3-1)

wherein $R^{10}$ to $R^{14}$ are a hydrogen atom.

10. The method for producing a 2-alkenylamine compound according to claim 1, wherein the Bronsted acid is selected from the group consisting of (i) halogenated hydrogens selected from the group consisting of hydrochloric acid, hydrogen fluoride, hydrogen bromide, and hydrogen iodide, (ii) sulfuric acid, (iii) sulfonic acids selected from the group consisting of methanesulfonic acid, p-toluenesulfonic acid, and trifluoromethane sulfonic acid, (iv) oxo acids of phosphorus selected from the group consisting of phosphoric acid, pyrophosphoric acid, polyphosphoric acid, phosphorous acid, and hypophosphorous acid, (v) carboxylic acids selected from the group consisting of acetic acid, trifluoroacetic acid, and benzoic acid, and (vi) boric acids selected from the group consisting of boric acid and phenylboric acid.

* * * * *